United States Patent [19]

Sato et al.

[11] Patent Number: 5,094,722
[45] Date of Patent: Mar. 10, 1992

[54] PROCESS FOR THE PURIFICATION OF A DIMETHYLPHENOL ISOMER

[75] Inventors: Toshio Sato, Ibaraki; Koji Tabata, Chofu; Toshihiko Kashitani, Ibaraki, all of Japan

[73] Assignee: Sumikin Chemical Co., Ltd., Tokyo, Japan

[21] Appl. No.: 568,053

[22] Filed: Aug. 16, 1990

[30] Foreign Application Priority Data

Oct. 11, 1989 [JP] Japan .................. 1-264237

[51] Int. Cl.⁵ .................. B01D 3/14; C07C 37/74; C07C 37/84
[52] U.S. Cl. .................. 203/47; 203/48; 568/751; 568/756
[58] Field of Search .................. 203/48, 47, 81; 568/751, 756, 749

[56] References Cited

U.S. PATENT DOCUMENTS

| 2,536,040 | 1/1951 | Davidson | 568/756 |
| 2,541,682 | 2/1951 | Arnold | 203/48 |
| 2,861,112 | 11/1958 | Christensen et al. | 568/751 |
| 4,447,658 | 5/1984 | Leston | 568/751 |

FOREIGN PATENT DOCUMENTS

| 143472 | 6/1985 | European Pat. Off. | 568/751 |
| 63-222137 | 9/1988 | Japan . | |
| 645446 | 11/1950 | United Kingdom | 568/756 |
| 1323066 | 7/1973 | United Kingdom | 568/756 |

Primary Examiner—Wilbur Bascomb, Jr.
Attorney, Agent, or Firm—Burns, Doane, Swecker & Mathis

[57] ABSTRACT

A purified desired isomer which is either 3,4- or 3,5-dimethylphenol is separated with a high yield from a dimethylphenol-containing fraction which contains both 3,4- and 3,5-dimethylphenols. The fraction is distilled so as to give a distillate which is enriched with the desired dimethylphenol isomer to be separated and which contains at least 35% by weight of the desired isomer. The desired DMP isomer is crystallized from a melt of the enriched distillate in two stages with at least part of the filtrate separated from the precipitated crystals in the second crystallization stage being circulated to the first crystallization stage. The enriched distillate is introduced into the first crystallization stage when it contains the desired isomer in a concentration of from 35% to less than 70% by weight, or it is introduced into the second crystallization stage when it contains the desired isomer in a concentration of 70% by weight or higher.

5 Claims, 2 Drawing Sheets

PROCESS FOR THE PURIFICATION OF A DIMETHYLPHENOL ISOMER

BACKGROUND OF THE INVENTION

1. Field of the Invention

This invention relates to a process for the purification of dimethylphenol. More particularly, it relates to a process for separating high-purity 3,4- or 3,5-dimethylphenol from a dimethylphenol-containing fraction by distillation and melt crystallization.

2. Description of the Prior Art

Dimethylphenol, which is also called xylenol or hydroxyxylene, is used as a starting material in the production of phenolic resins, medicines, pesticides, and the like. It is present in tar acids derived from coal tar fractions and has six isomers: 2,3-, 2,4-, 2,5-, 2,6-, 3,4-, and 3,5-isomers.

Many products are derived from coal tar by the following procedures. Coal tar is subjected to primary distillation to separate into several fractions, such as light oil, carbolic oil, naphthalene oil, wash oil (absorbing oil), and anthracene oil, leaving a soft pitch having a low softening point as a residue. Each fraction may be further subjected to appropriate separation or purification procedures such as distillation, extraction, and crystallization, as required, to recover the desired products.

Tar acids are obtained from various coal tar fractions such as carbolic oil, naphthalene oil, and wash oil by extracting these fractions with an aqueous sodium hydroxide solution and then neutralizing the resulting extract, which contains a tar acid as its sodium salt. Tar acids are mixtures of various phenolic compounds and are usually separated by fractional distillation into several fractions, e.g., phenol, o-methylphenol, m- and p-methylphenol, and dimethylphenol fractions.

The dimethylphenol fraction of a tar acid contains all or some of the six isomers of dimethylphenol as well as ethylphenols and trimethylphenols. The melting and boiling points of these compounds are shown in Table 1 below.

TABLE 1

| Compound (Abbrev.) | M.p. (°C.) | B.p. (°C.) |
| --- | --- | --- |
| 2,3-Dimethylphenol (2,3-DMP) | 72.6 | 216.9 |
| 2,4-Dimethylphenol (2,4-DMP) | 24.5 | 210.9 |
| 2,5-Dimethylphenol (2,5-DMP) | 74.9 | 211.1 |
| 2,6-Dimethylphenol (2,6-DMP) | 45.6 | 201.1 |
| 3,4-Dimethylphenol (3,4-DMP) | 65.1 | 226.9 |
| 3,5-Dimethylphenol (3,5-DMP) | 63.3 | 221.7 |
| 2-Ethylphenol (2-EP) | $<-18$ | 207.7 |
| 3-Ethylphenol (3-EP) | $-4.0$ | 214.0 |
| 4-Ethylphenol (4-EP) | 44.8 | 219.0 |

In order to use a compound in the dimethylphenol fraction as a starting material in a chemical synthesis, it is necessary to separate the compound from the fraction. However, it is very difficult to separate 3,4-dimethylphenol and 3,5-dimethylphenol individually since both the boiling points and melting points of these two isomers are close to each other, as shown in Table 1 above. Therefore, it is impossible to recover 3,4- or 3,5-dimethylphenol of high purity by rectification even if a special rectifying column with a great number of plates or a high reflux ratio is employed.

Commercial production of 3,4- and 3,5-dimethylphenols has had to rely on complicated chemical synthesis, and as a result, these substances are relatively expensive. Accordingly, there is a need for a process capable of separating 3,4- or 3,5-dimethylphenol of high purity from a dimethylphenol fraction of a tar acid or a similar source which contains both 3,4- and 3,5-dimethylphenols so as to obtain 3,4- or 3,5-dimethylphenol inexpensively and in large quantities.

Crystallization is also a well-known separation technique and is often employed when separation by distillation is difficult or inconvenient.

The present inventors attempted to separate 3,4- or 3,5-dimethylphenol by means of melt crystallization. Specifically, a dimethylphenol fraction obtained by distillation of a tar acid was rectified to recover a 3,4- or 3,5-dimethylphenol-rich fraction, which was then cooled with agitation to precipitate crystals of the desired 3,4- or 3,5-dimethylphenol, and the resulting slurry was centrifuged to separate the crystals from its mother liquor. However, it was found that this procedure could not provide 3,4- or 3,5-dimethylphenol crystals of high purity.

In Japanese Patent Application Kokai No. 63-222137(1988) the present inventors proposed that a dimethylphenol isomer of high purity can be separated from a dimethylphenol fraction by distilling the fraction so as to give a distillate which contains at least 35% by weight of the desired isomer to be separated and in which the concentration of each of the other dimethylphenol isomers is not greater than a prescribed value defined by inequality (I) given below, and then subjecting the distillate to crystallization from a melt, i.e., melt crystallization.

However, when the above-mentioned method is used to separate 3,4- or 3,5-dimethylphenol from a dimethylphenol fraction, the desired 3,4- or 3,5-isomer of high purity cannot be obtained from the distillate by melt crystallization and subsequent centrifugal separation unless the distillate contains at least 70% by weight of 3,4- or 3,5-isomer. This is because it is very difficult to completely remove the mother liquor from the crystals by means of centrifugal separation. In order to obtain the desired isomer of high purity, it is therefore necessary to wash the separated crystals with an organic solvent, such as hexane or heptane, which can readily dissolve the mother liquor. The use of an organic solvent, however, is not desirable from an ecological viewpoint and is disadvantageous in that it involves the steps of removing the solvent from the crystals and recovering the removed solvent, thereby making both the process and apparatus complicated. Furthermore, the yield of the desired isomer is greatly decreased by washing.

Other purification methods for dimethylphenols are disclosed in Japanese Patent Application Kokai Nos. 49-117435 (1974), 57-165333(1982), 58-52235(1983), 60-136528(1985), 60-248638(1985) and 63-303938(1988), as well as Japanese Patent Publication Nos. 52-38545(1977), 58-13527(1983), 58-58330 (1983), 61-31088(1986), 62-1933(1987), 63-6533(1988) and 63-6534(1988).

SUMMARY OF THE INVENTION

It is an object of this invention to provide a process for separating a purified 3,4- or 3,5-dimethylphenol isomer with a high yield from a mixture containing both of these isomers by distillation and melt crystallization.

Another object of the invention is to provide a purification process for 3,4- or 3,5-dimethylphenol which is capable of recovering 3,4- or 3,5-dimethylphenol of a purity of 99% or higher without washing.

These objects can be accomplished by performing melt crystallization in two stages after distillation according to the present invention.

In a process of the present invention, a high-purity 3,4-or 3,5-dimethylphenol is separated from a fraction containing both 3,4- and 3,5-dimethylphenols in which one is a desired dimethylphenol (DMP) isomer to be separated and the other is an undesired DMP isomer. The process comprises:

(a) distilling the fraction containing both 3,4- and 3,5-DMPs so as to give a distillate which is enriched with the desired DMP isomer, said enriched distillate containing at least 35% by weight of the desired DMP isomer and the concentration of the undesired DMP isomer being in the range defined by the following inequality:

$$U \leq (100-x)[P/(100-P)] \qquad (I)$$

wherein U is the concentration in weight percent of the undesired DMP isomer in the enriched distillate;

x is the concentration in weight percent of the desired DMP isomer therein; and

P is the concentration in weight percent of the desired DMP isomer in mother liquor in an solid-liquid equilibrium state at the temperature of first-stage melt crystallization;

(b) determining the concentration of the desired DMP isomer in the enriched distillate;

(c) introducing the enriched distillate in melt into a first stage melt crystallizer when the concentration of the desired DMP isomer in the enriched distillate is less than 70% by weight or into a second stage melt crystallizer when the concentration of the desired DMP isomer therein is 70% by weight or higher;

(d) performing first stage melt crystallization in the first stage melt crystallizer at a temperature below 20° C. to precipitate crude crystals of the desired DMP isomer;

(e) performing second stage melt crystallization in the second stage melt crystallizer at a temperature higher than that of the first stage melt crystallization to precipitate purified crystals of the desired DMP isomer;

(f) separating the crystals precipitated in step (d) from a filtrate and introducing the separated crude crystals into the second stage melt crystallizer after melting;

(g) separating the crystals precipitated in step (e) from a filtrate and recovering the separated purified crystals of the desired DMP isomer;

(h) circulating a part of the filtrate obtained in step (f) to the first stage melt crystallizer; and (i) circulating a part of the filtrate obtained in step (g) to the second stage melt crystallizer while the remainder thereof is circulated to the first stage melt crystallizer.

DETAILED DESCRIPTION OF THE INVENTION

Figure 1:
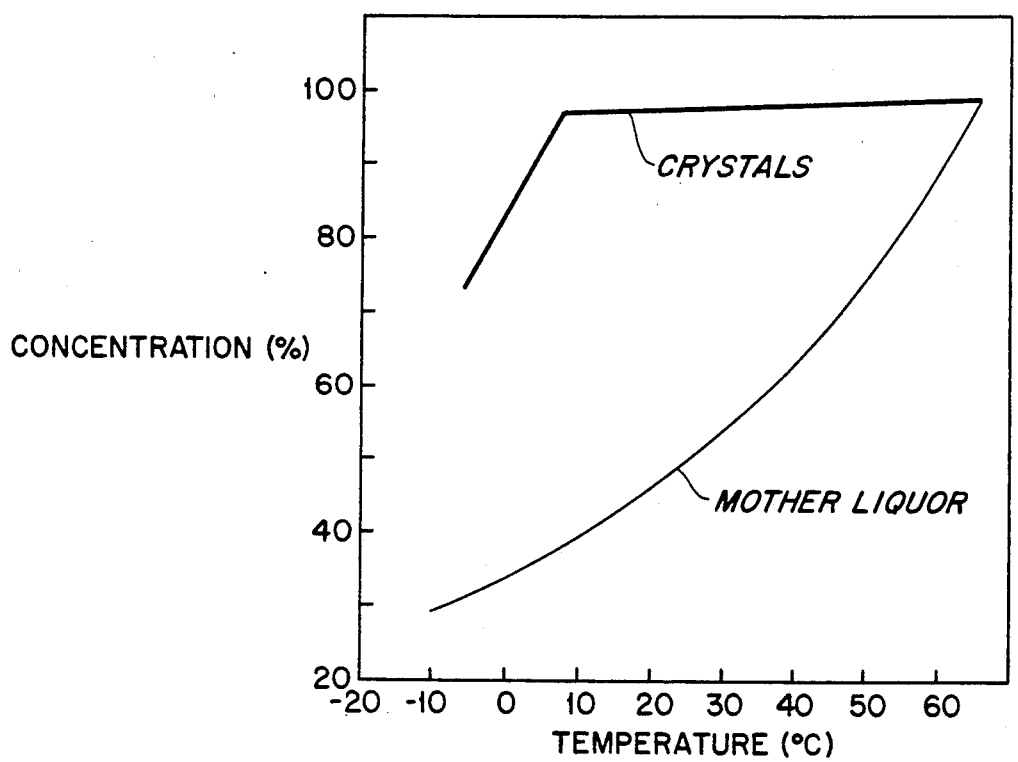
FIG. 1 is the solid-liquid equilibrium diagram of 3,4-dimethylphenol (3,4-DMP)

The fraction used in the invention contains both 3,4- and 3,5-dimethylphenols (3,4- and 3,5-DMPs) and is hereinafter referred to as a DMP-containing fraction for short. The DMP-containing fraction may be a dimethylphenol fraction obtained by distillation of a tar acid, which is in turn obtained from various coal tar fractions such as carbolic oil and naphthalene oil by extracting these fractions with an aqueous sodium hydroxide solution followed by neutralization. The DMP-containing fraction may be deriven from other sources as long as it contains 3,4- and 3,5-DMPs. For example, it may be derived from a synthetic phenol.

When the present invention is used to separate purified 3,4-DMP, the desired isomer is 3,4-DMP while 3,5-DMP is an undesired isomer. Similarly, when it is used to separate a purified 3,5-DMP, the desired isomer is 3,5-DMP and 3,4-DMP becomes an undesired isomer.

As mentioned previously, the boiling points and melting points of these isomers are close to each other. Therefore, mere distillation or melt crystallization of a DMP-containing fraction cannot separate the desired 3,4- or 3,5-DMP isomer of high purity.

According to the present invention, a DMP-containing fraction is initially distilled so as to give a distillate enriched with the desired DMP isomer to be separated, and the enriched distillate in melt is then subjected to melt crystallization to preferentially precipitate crystals of the desired DMP isomer which is present in the melt in a major amount while the undesired isomer which is present in a minor amount remains in molten state. The melt crystallization is performed in two stages in the present invention.

Figure 2:
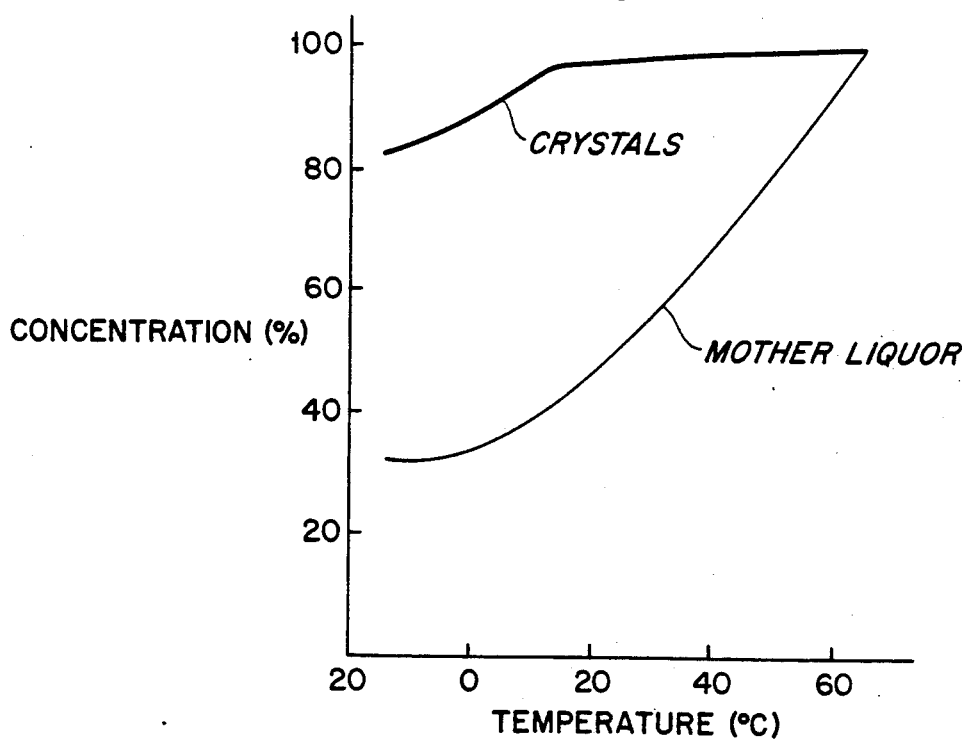
FIG. 2 is the solid-liquid equilibrium diagram of 3,5-dimethylphenol (3,5-DMP)

The key factor in melt crystallization is the solid-liquid equilibrium of the substances to be separated. FIGS. 1 and 2 show experimentally determined solid-liquid equilibrium diagrams for 3,4-DMP and 3,5-DMP, respectively. The curves for crystals in these figures indicate the purity of crystals recovered by centrifugation.

As is apparent from FIGS. 1 and 2, when the concentration of 3,4- or 3,5-DMP in a melt which is subjected to melt crystallization is below about 30% by weight, no crystals can be precipitated from the melt no matter how much the temperature is decreased. The quantity of crystals precipitated from a melt at a given temperature is directly proportional to the difference of the concentration of the desired DMP isomer in mother liquor at that temperature from the concentration thereof in the melt. In practice, the desired isomer should be present in the enriched distillate in an appreciably higher concentration than 30% in order to attain a significant yield. Therefore, the enriched distillate should contain at least 35% by weight of the desired isomer, and preferably at least 50% by weight of the desired isomer.

The similarity of the solid-liquid equilibrium diagrams for 3,4-DMP and 3,5-DMP indicates that these isomers resemble one another in their behavior during melt crystallization. In order to obtain crystals of the desired DMP isomer of high purity by melt crystallization, it is important to prevent the undesired isomer from crystallizing and thereby contaminating crystals of the desired isomer. For this purpose, according to the present invention, the concentration of the undesired isomer in the enriched distillate should be limited to the amount expressed by inequality (I). Thus, when the concentration of the undesired DMP isomer in the enriched distillate satisfies inequality (I) at the temperature of the first-stage melt crystallization, crystallization of the undesired DMP isomer can be minimized during the first-stage melt crystallization.

The value of P in inequality (I) is the concentration of the desired DMP isomer in mother liquor in an solid-liquid equilibrium state, which varies depending on the temperature and which can be determined from a solid-liquid equilibrium diagram such as FIGS. 1 or 2 for the desired isomer.

Accordingly, when the temperature of the first-stage melt crystallization is previously set, the value for P can be determined from the relationship as illustrated in FIGS. 1 or 2, which may be either recorded as a chart or stored in a computer memory. After P is determined, the relationship between the concentration of the desired isomer (x) in an enriched distillate and the maximum value for the concentration of the undesired isomer (U) allowable for the enriched distillate can be defined by inequality (I). According to the present invention, the distillation step is performed so as to obtain an enriched distillate for which the values of x and U satisfy inequality (I).

Alternatively, when an enriched distillate has already been obtained, the values for U and x are determined. Therefore, the minimum value for P can be calculated from inequality (I). In this case, the first-stage melt crystallization is carried out above the temperature corresponding to the minimum value for P.

Thus, according to the present invention, the conditions for distillation or the temperature of the first-stage melt crystallization is restricted so as to satisfy inequality (I).

The distillation of the DMP-containing fraction is carried out in a conventional manner either batchwise, continuously, or by a combination of batchwise distillation and continuous distillation. The pressure may be subatmospheric, atmospheric or superatmospheric.

When the desired isomer is 3,4-DMP, in order to obtain an enriched distillate having a minimized content of the undesired 3,5-isomer, it is preferable to perform the distillation while taking precautions to prevent incorporation of lower-boiling contaminants in the distillate. On the other hand, when the desired isomer is 3,5-DMP, precautions are preferably taken to prevent incorporation of higher-boiling contaminants in the enriched distillate.

The enriched distillate containing at least 35% by weight of the desired DMP isomer is then subjected to melt crystallization in two stages in which crude crystals of the desired isomer obtained in the first stage are subjected again to melt crystallization in the second stage. A part of the filtrate separated from the crystals in the first-stage melt crystallization is circulated to the first stage, while a part of the filtrate separated from the crystals in the second stage is circulated to the second-stage melt crystallization and the remainder thereof is circulated to the first-stage. If melt crystallization is performed in a single stage, it is difficult to separate the desired DMP isomer of high purity with a high yield.

When the concentration of the desired DMP isomer in the enriched distillate is in the range of from 35% to less than 70% by weight, the enriched distillate is introduced into a melt crystallizer in the first stage and the crystals obtained in the first stage are then subjected to melt crystallization again in the second stage, thereby making it possible to separate the desired isomer having a purity of 99% by weight or higher with a satisfactory yield. If such an enriched distiallate is introduced into the second crystallization stage, it is not possible to obtain the desired isomer of high purity with a high yield.

On the other hand, when the enriched distillate contains 70% by weight or more of the desired isomer, highly pure crystals of the desired isomer can be separated by introducing the enriched distillate directly into a melt crystallizer in the second stage without subjecting it to melt crystallization in the first stage. In this case, if the enriched distillate is introduced into the first crystallization stage, it leads to increased operating costs and therefore is disadvantageous.

Therefore, prior to melt crystallization, the concentration of the desired DMP isomer in the enriched distillate is determined by a suitable analytical method in order to decide into which stage of melt distillation the enriched distillate should be introduced.

In general, melt crystallization of 3,4- or 3,5-DMP can be performed in the range of from $-20°$ to $+60°$ C. Melt crystallization involves heating a material to form a melt and cooling and maintaining the melt at a melt crystallization temperature in a crystallizer for a period sufficient to precipitate a satisfactory amount of crystals from the melt. The heating is preferably continued until the material is entirely melted, although a partial melt may be employed as long as the fluidity is sufficient to enable smooth pumping. The residence time of the melt in the crystallizer can be determined on the basis of the desired yield of crystals and operating efficiency.

According to the present invention, the first-stage melt crystallization is performed at a temperature below $20°$ C. and preferably below $10°$ C. The second-stage melt crystallization is performed at a temperature higher than the temperature of the first-stage melt crystallization.

When the first-stage melt crystallization is performed at a temperature above $20°$ C., the amount of crystals precipitating in the first-stage melt crystallization is undesirably decreased and the operating efficiency is decreased. In order to improve the operating efficiency and the yield of the desired isomer, a melt of the enriched distillate may be cooled to as low as $-20°$ C. or lower to recover crude crystals of the desired isomer as much as possible in the first stage.

In the second-stage melt crystallization, as the crystallization temperature is increased, the purity of crystals separated from the melt increases but the yield thereof decreases. Therefore, the temperature of the secondstage melt crystallization can be set in accordance with the concentration of the desired DMP isomer in the melt to be treated and the desired purity of the purified product. When the temperature of the second-stage melt crystallization is lower than $20°$ C., the resulting crystals are too fine so that the separation of the crystals from the remaining melt (mother liquor) by centrifugation becomes worse and hence the purity of the recovered crystals is lowered, as can be seen from FIGS. 1 and 2. Therefore, if it is desired to recover purified crystals having a purity of 99% or higher, the temperature of the second-stage melt crystallization should be above $20°$ C. and preferably above $30°$ C.

The concentration of the resulting slurry, i.e., the concentration of crystals in the melt formed by crystallization in each stage of melt crystallization should be in the range of 15 to 40% by weight and preferably in the range of 20 to 30% by weight. If the slurry concentration exceeds 40% by weight, it is difficult to pump the slurry. A slurry concentration of less than 15% by weight reduces the operating efficiency. The slurry concentration can be adjusted by controlling the proportion of the filtrate circulated to the melt crystallizer.

The crystals precipitated in the first and second stages can be collected by any suitable technique. It is usually convenient to employ a centrifugal filter. The crystals collected in the second-stage melt crystallization are highly pure, so they need not be washed with an organic solvent to further improve the purity.

A part of the filtrate separated from the purified crystals of the desired DMP isomer in the second stage is circulated to the second-stage melt crystallizer in an amount sufficient to maintain the slurry concentration in the second-stage crystallizer at a level within the above-mentioned range. The remainder of the filtrate in the second stage is circulated to the first-stage melt crystallizer.

Likewise, a part of the filtrate separated from the precipitated crude crystals in the first crystallization stage is circulated to the first-stage melt crystallizer in such an amount that the the slurry concentration in the first-stage crystallizer is maintained at a level within the above-mentioned range. The remainder thereof is withdrawn from the melt crystallization apparatus and may be either discarded or redistilled to form an enriched distillate.

By performing the distillation and melt crystallization in the above manner, purified 3,4- or 3,5-DMP crystals having a purity of 99% or more can be recovered with a high yield from a fraction which contains both 3,4- and 3,5-DMPs. In particular, by employing a two-stage melt crystallization, it is possible to constantly recover the desired DMP isomer of high purity even if the concentration of the desired DMP isomer in the enriched distillate is less than 70% by weight. Therefore, the load to be applied to the distillation step can be significantly reduced.

An embodiment of the process of the present invention will now be described while referring to FIG. 3.

Figure 3:
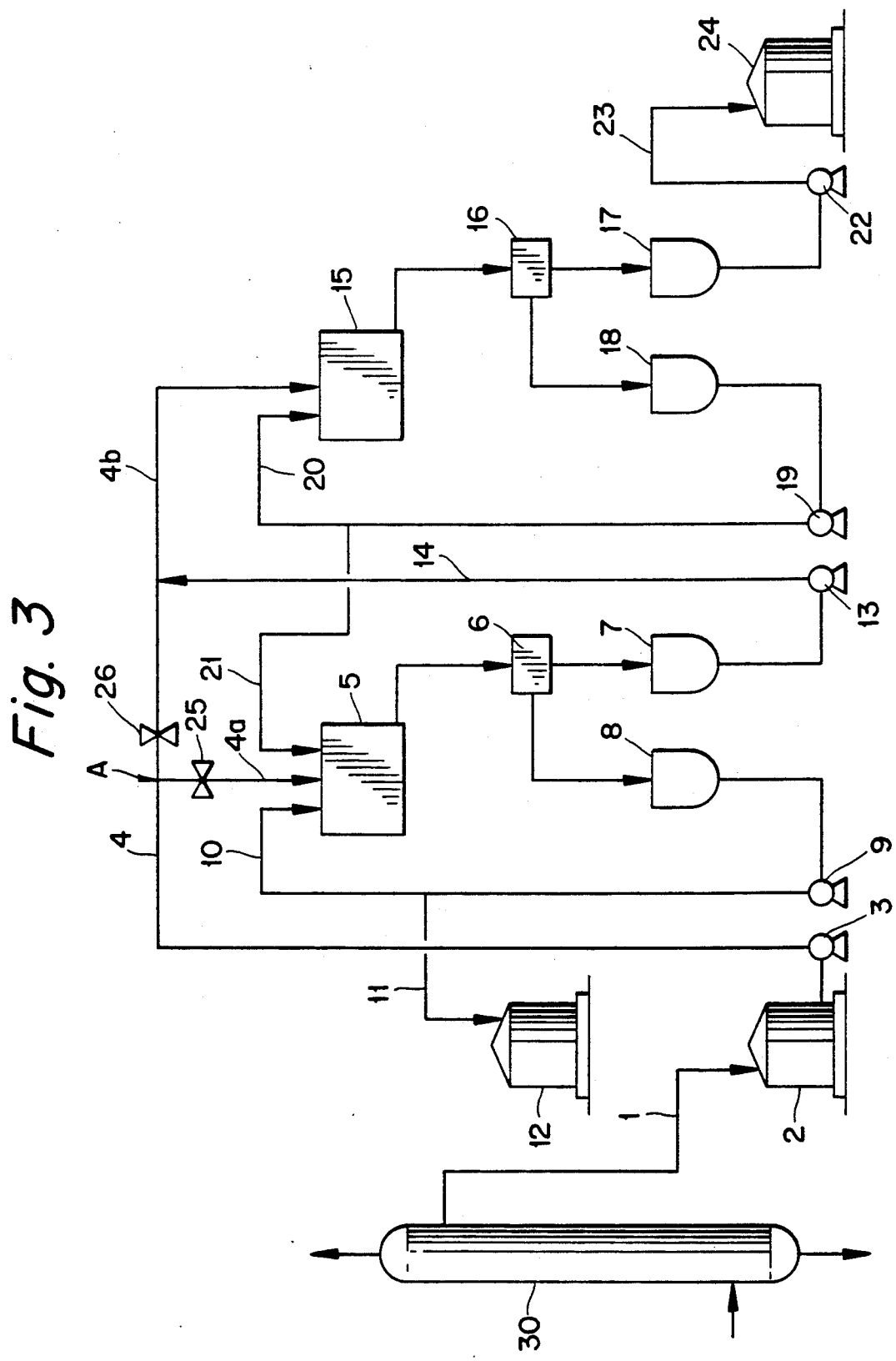
FIG. 3 is a flow diagram for a two-stage crystallization apparatus suitable for use in practice of the present invention.

FIG. 3 is a flow diagram of continuous two-stage crystallization according to the present invention.

In FIG. 3, an enriched distillate obtained by the preceding distillation step in distillation column 30 which contains at least 35% by weight of the desired isomer selected from 3,4- and 3,5-DMP and an amount of the other undesired DMP isomer satisfying the conditions defined by inequality (I) is introduced in molten state through line 1 into an enriched distillate tank 2, from which it is continuously fed by means of a pump 3 through a feed line 4 to either a first-stage crystallizer 5 or a second-stage crystallizer 15. The switching of the crystallizer to which the enriched distillate is fed is achieved by means of valves 25 and 26 depending on the concentration of the desired DMP isomer in the distillate, the concentration being determined by sampling the distillate at an appropriate position prior to these valves, e.g., in feed line 4. When the concentration of the desired isomer is less than 70% by weight, valve 25 is opened and valve 26 is closed, allowing the distillate to pass into the first-stage crystallizer 5 through a line 4a. On the other hand, when it is 70% by weight or higher, valve 25 is closed and valve 26 is opened, allowing the distillate to pass into the second-stage crystallizer 15 through a line 4b.

A part of a filtrate separated in a first-stage solid liquid separator (filter) 6, which is circulated by means of a pump 9 through a filtrate circulating line 10, and a part of a filtrate separated in a second-stage solid-liquid separator (filter) 16, which is circulated through a second-stage filtrate feeding line 21, are also continuously fed into the first-stage crystallizer 5. The first-stage and second-stage solid-liquid separators 6 and 16 may be centrifugal filters.

The contents of the first stage crystallizer 5 are cooled to a predetermined temperature below 20° C. and maintained at that temperature while being agitated by an agitater (not shown) so as to crystallize the desired DMP isomer with which the DMP-containing fraction is enriched. The amount of precipitated crystals is increased as the temperature in the first stage crystallizer is decreased. However, if the temperature is lower than that defined by inequality (I), the precipitated crystals will be appreciably contaminated with an undesired isomer, leading to a decrease in purity of the desired DMP isomer. Therefore, the temperature in the first stage crystallizer should be equal to or higher than that defined in inequality (I).

The slurry formed in the first stage crystallizer is continuously withdrawn and passed into the first-stage filter 6 to separate the precipitated crude crystals from the filtrate. The crystals are then passed into a melting tank 7, while the filtrate is passed into a first-stage filtrate tank 8, from which a part of the filtrate is circulated to the first-stage crystallizer 5 through the filtrate-circulating line 10 with the remainder being withdrawn through a line 11 into a filtrate tank 12. The filtrate may be recycled to a distillation column (not shown) to obtain the enriched distillate.

The crude crystals separated in the first-stage filter 6 and melted in the melting tank 7 are continuously fed by means of a pump 13 through line 14 into the second-stage crystallizer 15. A part of the filtrate separated in the second-stage filter 16 and passed into a second-stage filtrate tank 18 is also continuously fed into the second-stage crystallizer 15 by means of a pump 19 through a filtrate-circulating line 20.

The contents of the second-stage crystallizer 15 are cooled to a predetermined temperature which is higher than the first-stage crystallization temperature and maintained at that temperature while being agitated by an agitater (not shown) so as to crystallize the desired DMP isomer. The slurry formed in the second-stage crystallizer is continuously withdrawn and passed into the second-stage filter 16 to separate the precipitated purified crystals from the filtrate. The crystals are then passed into a second-stage melting tank 17, while the filtrate is passed into the second-stage filtrate tank 18, from which a part of the filtrate is circulated to the second-stage crystallizer 15 through the filtrate circulating line 20, and the remainder is circulated to the first-stage crystallizer 5 through the filtrate-circulating line 21.

The purified crystals separated in the second-stage filter 16 and melted in the melting tank 17 are passed by means of a pump 22 through a product withdrawal line 23 into a product tank 24 in which it is stored until shipment.

The following examples are presented as specific illustrations of the claimed invention. It should be understood, however, that the invention is not limited to the details set forth in the examples.

EXAMPLE 1

A DMP fraction obtained by distillation of a crude tar acid which was produced from coal tar fractions by alkali extraction followed by neutralization was distilled so as to give a distillate enriched with 3,5-DMP. The enriched distillate having the composition indicated in Table 2 satisfied inequality (I) when the crystallization temperature was set at −17.5° C.

The enriched distillate containing 55% by weight of 3,5-DMP was processed as shown in FIG. 3 for purification.

Specifically, the enriched distillate which was pooled in the enriched distillate tank 2 at a temperature of about 60° C. was continuously pumped into the first-stage crystallizer 5 at a flow rate of 100 kg/hr and mixed therein with a part of the first stage filtrate, which was fed through the filtrate circulating line 10 at a flow rate of 139.8 kg/hr, and a part of the second stage filtrate, which was fed through the filtrate-circulating line 21 at a flow rate of 47.9 kg/hr. The mixture in the first-stage crystallizer 5 was cooled and kept at a temperature of −17.5° C. while being agitated to precipitate crystals of the desired 3,5-DMP isomer.

The slurry formed in the first-stage crystallizer 5 was withdrawn at a rate of 287.7 kg/hr so as to maintain a constant level in the crystallizer 5. The withdrawn slurry was passed to the first-stage filter 6, from which crude 3,5-DMP crystals were separated at a rate of 82.2 kg/hr. The separated crude crystals were passed to the first-stage melting tank 7 and heated therein to a temperature of 70° C. for melting. The filtrate obtained in the filter 6 at a rate of 205.5 kg/hr was passed to the filtrate tank 8, from which a part thereof was circulated to the first stage crystallizer at a rate of 139.8 kg/hr as mentioned above, while the remainder (65.7 kg/hr) was withdrawn from the filtrate tank 8 and pooled in the filtrate tank 12.

The crude 3,5-DMP melted in the first-stage melting tank 7 was fed at a flow rate of 82.2 kg/hr into the second-stage crystallizer 15 and mixed therein with a part of the second-stage filtrate, which was circulated to the second-stage crystallizer 15 through a filtrate-circulating line 20 at a flow rate of 49.3 kg/hr. In the second-stage crystallizer 15, the mixture was kept at a temperature of 42° C. while being agitated so as to precipitate and grow 3,5-DMP crystals.

The slurry formed in the second-stage crystallizer 15 was withdrawn at a rate of 131.5 kg/hr so as to maintain a constant level in the crystallizer 15. The withdrawn slurry was passed to the second-stage filter 16, in which purified 3,5-DMP crystals as a product were separated from the second stage filtrate. The purified crystals and the filtrate were recovered at a rate of 34.3 kg/hr and 97.2 kg/hr, respectively.

The purified 3,5-DMP crystals were melted in the second-stage melting tank 17 and temporarily stored in the product tank 24 until shipment.

The second-stage filtrate was passed to the filtrate tank 18, from which a part thereof was circulated to the second-stage crystallizer 15 at a rate of 49.3 kg/hr, while the remainder (47.9 kg/hr) was circulated to the first-stage crystallizer 5 as mentioned above.

The compositions of the mixture, separated crystals, and filtrate in each crystallization stage are also shown in Table 2.

TABLE 2

| Compound[1)] | Compositions by weight percent | | | | |
|---|---|---|---|---|---|
| | 3,5-DMP | 3,4-DMP | m-EP | p-EP | Others |
| Enriched Distillate | 55.0 | 7.3 | 9.2 | 7.1 | 21.4 |
| First Stage | | | | | |
| Mixture | 46.3 | 8.6 | 11.1 | 8.3 | 25.7 |
| Crude Crystals | 79.6 | 3.1 | 4.4 | 3.3 | 9.6 |
| Filtrate | 32.0 | 10.8 | 14.1 | 10.4 | 32.7 |
| Second Stage | | | | | |
| Mixture | 76.0 | 3.7 | 5.1 | 3.7 | 11.5 |
| Purif. Crystals | 99.0 | 0.1 | 0.1 | 0.1 | 0.7 |
| Filtrate | 70.0 | 4.6 | 6.3 | 4.5 | 14.6 |

[1)]m-EP = m-ethylphenol; p-EP = p-ethylphenol.

As can be seen from Table 2, 3,5-DMP having a purity of 99% by weight could be separated from an enriched distillate coltaining 55% by weight of 3,5-DMP with a yield of 61.7%.

EXAMPLE 2

A DMP fraction obtained by distillation of a crude tar acid which was prepared from coal tar fractions by alkali extraction followed by neutralization was distilled so as to give a distillate enriched with 3,4-DMP. The enriched distillate having the composition indicated in Table 3 satisfied inequality (I) when the crystallization temperature was set at −17° C. The enriched distillate was purified by processing as shown in FIG. 3.

The enriched distillate containing 80.6% 3,4-DMP which was pooled in the enriched distillate tank 2 at a temperature of about 80° C. was continuously pumped into the second-stage crystallizer 15 at a flow rate of 100 kg/hr together with a flow of crude 3,4-DMP at a rate of 156.9 kg/hr which had been crystallized in the first-stage crystallizer 5, separated in the first-stage filter 6 and melted in the melting tank 7. A part of the second-stage filtrate was also fed into the second stage crytallizer 15 through a filtrate circulating line 20 at a flow rate of 160.7 kg/hr. The mixture in the second-stage crystallizer 15 was kept at a temperature of 42° C. while being agitated so as to precipitate and grow 3,4-DMP crystals.

The slurry formed in the second-stage crystallizer 15 was withdrawn at a rate of 417.6 kg/hr. The withdrawn slurry was passed to the second stage filter 16, in which it was separated into purified 3,4-DMP crystals as a product and a second stage filtrate. The purified crystals and the filtrate were recovered at a rate of 71.6 kg/hr and 346.0 kg/hr, respectively.

The purified crystals of 3,4-DMP were melted in the second stage melting tank 17 and temporarily stored in the product tank 24 until shipment.

The second-stage filtrate was passed to the filtrate tank 18, from which a part thereof was circulated to the second-stage crystallizer 15 at a rate of 160.7 kg/hr as mentioned above, while the remainder (185.3 kg/hr) was circulated to the first-stage crystallizer 5.

In the first-stage crystallizer 5, the above-mentioned circulation flow from the second-stage crystallizer was mixed with a part of the filtrate separated in the first-stage filter 6 and circulated through the filtrate circulating line 10 at a flow rate of 363.9 kg/hr. The mixture was kept at −17° C. while being agitated to precipitate 3,4-DMP crystals.

The slurry formed in the first-stage crystallizer 5 was withdrawn at a rate of 549.2 kg/hr and passed to the first stage filter 6, in which crude 3,4-DMP crystals were separated at a rate of 156.9 kg/hr from the filtrate. The separated crude crystals were passed to the first-stage melting tank 7, melted therein at a temperature of about 70° C., and fed into the second-stage crystallizer 15. The filtrate obtained in the filter 6 at a rate of 392.3 kg/hr was passed to the filtrate tank 8, from which a part thereof was circulated to the first-stage crystallizer at a rate of 363.9 kg/hr as mentioned above, while the remainder (28.4 kg/hr) was withdrawn into the filtrate tank 12.

The compositions of the mixture, separated crystals, and filtrate obtained in each stage are also shown in the following Table 3.

TABLE 3

| Compound[1] | Compositions by weight percent | | | | |
|---|---|---|---|---|---|
| | 3,5-DMP | 3,4-DMP | m-EP | p-EP | Others |
| Enriched Distillate | 2.1 | 80.6 | 4.0 | 2.3 | 10.6 |
| First Stage | | | | | |
| Mixture | 6.9 | 44.8 | 11.7 | 6.6 | 30.9 |
| Crude Crystals | 2.1 | 79.6 | 4.1 | 2.6 | 11.6 |
| Filtrate | 7.5 | 32.0 | 14.3 | 8.2 | 38.0 |
| Second Stage | | | | | |
| Mixture | 2.5 | 76.2 | 5.0 | 2.9 | 13.4 |
| Purif. Crystals | 0.1 | 99.0 | 0.2 | 0.1 | 0.6 |
| Filtrate | 3.1 | 70.0 | 6.5 | 3.5 | 16.9 |

[1] m-EP = m-ethylphenol; p-EP = p-ethylphenol.

As can be seen from Table 3, the enriched distillate containing 80% by weight of 3,4-DMP could be purified so as to have a purity of 99% by weight by introducing it into the second stage crystallizer 15 without passing it through the first stage crystallizer 5 and circulating a part of the filtrate from the second stage filter 16 to the first stage crystallizer. The yield of the purified product was 88%.

Although the present invention has been described with respect to preferred embodiments, it is to be understood that variations and modifications may be employed without departing from the concept of the invention as defined in the following claims.

What is claimed is:

1. A process for separating a purified 3,4- or 3,5-dimethylphenol from a fraction containing both 3,4- and 3,5-dimethylphenols in which one is a desired dimethylphenol isomer to be separated and the other is an undesired isomer, by distillation and subsequent melt crystallization in two stages, comprising:

(a) distilling the fraction containing both 3,4- and 3,5-dimethylphenols so as to give a distillate which is enriched with the desired dimethylphenol isomer, said enriched distillate containing at least 35% by weight of the desired isomer and the concentration of the undesired dimethylphenol isomer being in the range defined by the following inequality:

$$U \leq (100-x)[P/(100-P)] \quad (I)$$

wherein U is the concentration in weight percent of the undesired dimethylphenol isomer in the enriched distillate;

x is the concentration in weight percent of the desired dimethylphenol isomer therein; and P is the concentration in weight percent of the desired dimethylphenol isomer in mother liquor in a solid-liquid equilibrium state at the temperature of first-stage melt crystallization;

(b) determining the concentration of the desired dimethylphenol isomer in the enriched distillate;

(c) introducing the enriched distillate in a melt state into a first stage melt crystallizer when the concentration of the desired dimethylphenol isomer in the enriched distillate is less than 70% by weight or into a second stage melt crystallizer when the concentration of the desired dimethylphenol isomer therein is 70% by weight or higher;

(d) performing first stage melt crystallization in the first stage melt crystallizer at a temperature below 20° C. to precipitate crude crystals of the desired isomer;

(e) performing second stage melt crystallization in the second stage melt crystallizer at a temperature higher than that of the first stage melt crystallization to precipitate purified crystals of the desired isomer;

(f) separating the crystals precipitated in step (d) by filtration from a filtrate and introducing the separated crude crystals into the second stage melt crystallizer after melting;

(g) separating the crystals precipitated in step (e) by filtration from a filtrate and recovering the separated purified crystals of the desired dimethylphenol isomer;

(h) circulating a part of the filtrate obtained in step (f) to the first stage melt crystallizer; and (i) circulating a part of the filtrate obtained in step (g) to the second stage melt crystallizer while the remainder thereof is circulated to the first stage melt crystallizer.

2. The process as claimed in claim 1 wherein the desired dimethylphenol isomer is 3,4-dimethylphenol and the undesired isomer is 3,5-dimethylphenol.

3. The process as claimed in claim 1 wherein the desired dimethylphenol isomer is 3,5-dimethylphenol and the undesired isomer is 3,4-dimethylphenol.

4. The process as claimed in claim 1 wherein the dimethylphenol-containing fraction is a fraction obtained by distillation of a tar acid.

5. The process as claimed in claim 1 wherein the precipitated crystals are separated by means of a centrifugal filter in steps (f) and (g).

* * * * *